(12) United States Patent
Sellers

(10) Patent No.: US 7,644,520 B2
(45) Date of Patent: *Jan. 12, 2010

(54) DETACHABLE SOLE FOR AN ANKLE AND FOOT COVERING

(76) Inventor: David R. Sellers, 3305 County Rd. 96, Ward, CO (US) 80481

( * ) Notice: Subject to any disclaimer, the term of this patent is extended or adjusted under 35 U.S.C. 154(b) by 368 days.

This patent is subject to a terminal disclaimer.

(21) Appl. No.: 11/259,168

(22) Filed: Oct. 25, 2005

(65) Prior Publication Data

US 2006/0196086 A1 Sep. 7, 2006

Related U.S. Application Data

(63) Continuation-in-part of application No. 11/189,204, filed on Jul. 25, 2005.

(60) Provisional application No. 60/659,991, filed on Mar. 7, 2005.

(51) Int. Cl.
*A43B 13/00* (2006.01)
*A43C 13/02* (2006.01)

(52) U.S. Cl. .............................. 36/103; 36/15; 36/132; 36/117.4

(58) Field of Classification Search .................. 36/7.5, 36/7.6, 117.4, 117.3, 132, 135, 37, 103, 123, 36/106, 15; D2/914
See application file for complete search history.

(56) References Cited

U.S. PATENT DOCUMENTS

| 995,245 | A | * | 6/1911 | Futterknecht | .................. 36/73 |
| 3,964,761 | A | | 6/1976 | Syrovatka | |
| 3,965,586 | A | | 6/1976 | Roosli | |
| 3,971,144 | A | | 7/1976 | Brugger-Stuker | |
| 4,123,854 | A | | 11/1978 | Pasich | |
| D250,796 | S | | 1/1979 | DeFever | |
| 4,156,316 | A | | 5/1979 | DeFever | |
| 4,160,301 | A | * | 7/1979 | Woolley | ..................... 12/120.5 |
| 4,199,880 | A | * | 4/1980 | Frey | ............................ 36/132 |
| 4,228,602 | A | | 10/1980 | Groves | |
| 4,269,430 | A | | 5/1981 | Eie | |
| 4,286,397 | A | | 9/1981 | Booty | |
| 4,291,473 | A | | 9/1981 | Sartor | |
| D263,516 | S | | 3/1982 | Booty | |
| 4,403,789 | A | | 9/1983 | Hickey | |
| 4,461,104 | A | * | 7/1984 | Calkin et al. | ................... 36/132 |
| D277,899 | S | | 3/1985 | Hutchinson | |
| 4,505,057 | A | | 3/1985 | Kiester | |
| 4,542,599 | A | * | 9/1985 | Annovi | ...................... 36/117.4 |

(Continued)

*Primary Examiner*—Jila M Mohandesi
(74) *Attorney, Agent, or Firm*—Daniel P. Dooley; Fellers, Snider, et al.

(57) ABSTRACT

A combination that preferably includes at least: a ski boot; a detachable sole detachably attached to the ski boot; and a detachable sole storage rack attached to the ski boot for use in storing the detachable sole when detached from the ski boot is disclosed. The detachable sole preferably includes at least: heel and toe chassis portions each formed from a baffled support matrix and overmolded with tread portions; and a latch assembly for securing the baffled support matrix adjacent the ski boot. The ski boot preferably provides a contoured heel portion and the latch assembly preferably incorporates a catch configured to conform to the contoured heel portion, a catch support interacting with the catch; a chassis attachment member communicating with said chassis; and an adjustment member interposed between said catch support and said chassis attachment member to accommodate a snug conformance of the catch adjacent the heel portion.

15 Claims, 17 Drawing Sheets

U.S. PATENT DOCUMENTS

| | | |
|---|---|---|
| 4,727,662 A | 3/1988 | Ilon |
| 4,774,775 A | 10/1988 | Pruitt |
| 4,843,672 A | 7/1989 | Fasse |
| 4,958,445 A | 9/1990 | Brisco |
| 5,283,963 A * | 2/1994 | Lerner et al. .................... 36/28 |
| 5,313,717 A * | 5/1994 | Allen et al. ..................... 36/28 |
| 5,369,896 A * | 12/1994 | Frachey et al. ................. 36/29 |
| 5,569,173 A | 10/1996 | Varn |
| 5,649,374 A * | 7/1997 | Chou ............................. 36/27 |
| 5,746,016 A | 5/1998 | Freisinger et al. |
| 5,815,953 A | 10/1998 | Kaufman et al. |
| 5,891,067 A | 4/1999 | Reed |
| 5,961,477 A | 10/1999 | Turtzo |
| 6,044,578 A | 4/2000 | Kelz |
| 6,277,087 B1 | 8/2001 | Hess et al. |
| 6,301,804 B1 | 10/2001 | Battaglia |
| 6,361,514 B1 | 3/2002 | Brown et al. |
| 6,402,183 B1 * | 6/2002 | Marmonier et al. ......... 280/613 |
| 6,421,935 B1 | 7/2002 | Bartlett |
| 6,481,121 B1 * | 11/2002 | Tucker .......................... 36/62 |
| 6,523,280 B1 | 2/2003 | Lapointe |
| 6,857,202 B2 * | 2/2005 | Pfander ....................... 36/3 R |
| 2002/0189133 A1 | 12/2002 | Parisotto et al. |

* cited by examiner

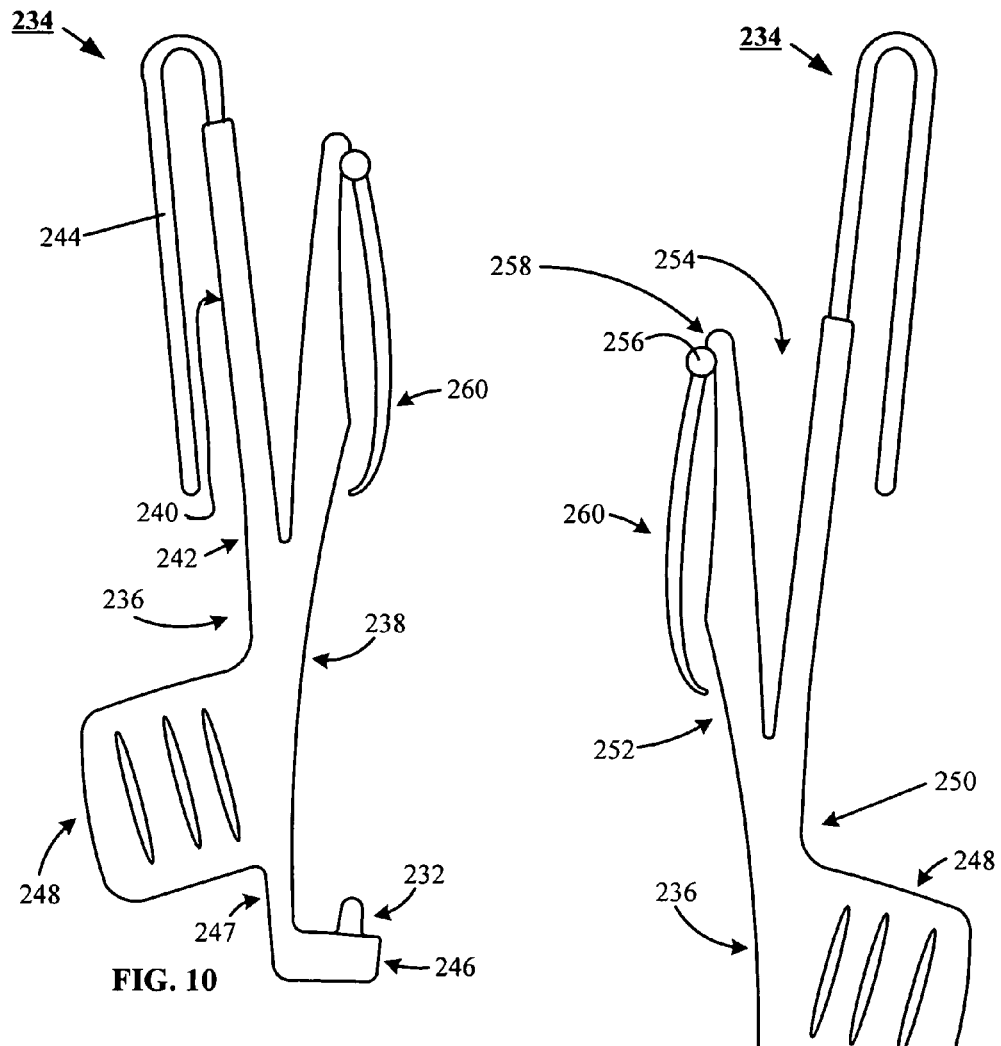
FIG. 10
FIG. 11
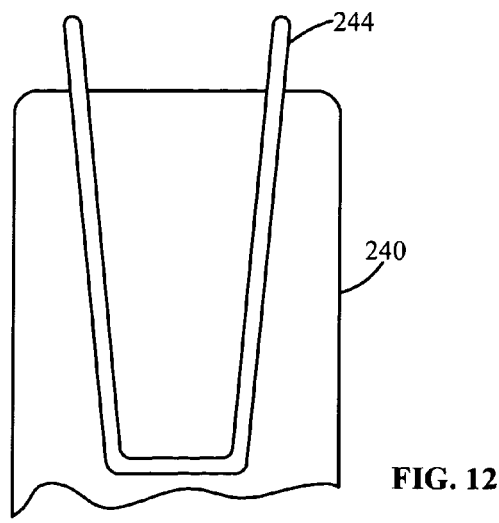
FIG. 12

DETACHABLE SOLE FOR AN ANKLE AND FOOT COVERING

RELATED APPLICATIONS

This application is a continuation-in-part of U.S. patent application Ser. No. 11/189,204 filed Jul. 25, 2005, entitled DETACHABLE SOLE FOR ANKLE AND FOOT COVERING, which claims priority to U.S. Provisional Application No. 60/659,991 filed Mar. 7, 2005, entitled SKI BOOT ATTACHMENTS.

FIELD OF THE INVENTION

This invention relates to detachable soles for ankle and foot coverings, which afford easier walking for individuals wearing ankle and foot coverings, and more particularly, but not by way of limitation, to attachments that easily attach and detach to the bottoms of ski boots, and to the bottom of an orthopedic device affixed to an individual's ankle and foot.

BACKGROUND

Walking in orthopedic devices or ski boots is an awkward endeavor at best. Attachments that fit onto the bottom of ski boots and orthopedic devices have been proposed in the prior art. However, each proposed solution has drawbacks, which fail to provide: an overall solution to ease the process of walking in ski boots or orthopedic devices when encountering changes in the walking terrain; and a convenient, compact configuration for storing the attachment when not in use.

As such, challenges remain and a need persists for improvements in methods and apparatuses for use in enhancing the walking experience of individuals wearing ski boots or orthopedic devices.

BRIEF SUMMARY OF THE INVENTION

In accordance with preferred embodiments, a combination including: an ankle and foot covering; a detachable sole configured for attachment to and detachment from the ankle and foot covering; a detachable sole storage rack configured for attachment to the ankle and foot covering and for receipt of the detachable sole, when the detachable sole is detached from the ankle and foot covering; and methods of making and using the combination are provided.

In a preferred embodiment, the detachable sole includes at least a chassis that provides a baffled support matrix interposed between top and bottom chassis portions, and more preferably the chassis includes a hinge interposed between a heel chassis portion and a toe chassis portion, in which said heel and toe chassis portions each comprise baffled support matrices interposed between top and bottom chassis portions to form the chassis.

Preferably, the toe chassis portion is overmolded with a toe tread portion to form a first sole portion, and the heel chassis portion is overmolded with a heel tread portion to form a second sole portion, and the hinge includes at least one hinge knuckle and a pair of hinge pins. Preferably, each hinge knuckle provides a pair of hinge pin apertures, and the hinge pins are configured for sliding engagement with the hinge pin apertures.

The detachable sole further preferably includes a latch assembly attached to the baffled support matrix and configured for securement of baffled support matrix adjacent said ankle and foot covering. In a preferred embodiment, the ankle and foot covering provide a contoured heel portion, and the latch assembly includes at least a catch configured to conform to the contoured heel portion, a catch support interacting with the catch, a chassis attachment member communicating with the baffled support matrix of said chassis, and an adjustment member interposed, between the catch support and the chassis attachment member, and configured to accommodate a snug conformance of the catch adjacent the heel portion.

In a preferred embodiment of the present invention, the catch support and attachment member each provide a threaded portion, which interact with the adjustment member to form the latch assembly. In a preferred embodiment, the adjustment member is a right-hand coil spring, and the threaded portion provided by each the attachment member and the catch support presents left-hand threads. The presentation of left-hand threads on opposing members promotes advancement of the preferred right-hand coil spring onto each the attachment member and the catch support.

These and various other features and advantages that characterize the claimed invention will be apparent upon reading the following detailed description and upon review of the associated drawings.

BRIEF DESCRIPTION OF THE DRAWINGS

FIG. 10 is a first side elevational view of an inventive detachable sole storage rack configured for interaction with the inventive detachable sole of FIG. 2.

FIG. 11 is a second side elevational view of the inventive detachable sole storage rack of FIG. 10.

FIG. 12 is a partial cutaway rear elevational view of the inventive detachable sole storage rack of FIG. 10.

DETAILED DESCRIPTION

Reference will now be made in detail to one or more examples of the invention depicted in the figures. Each example is provided by way of explanation of the invention, and not meant as a limitation of the invention. For example, features illustrated or described as part of one embodiment may be used with another embodiment to yield still a different embodiment. Other modifications and variations to the described embodiments are also contemplated within the scope and spirit of the invention.

Figures 1, 2:
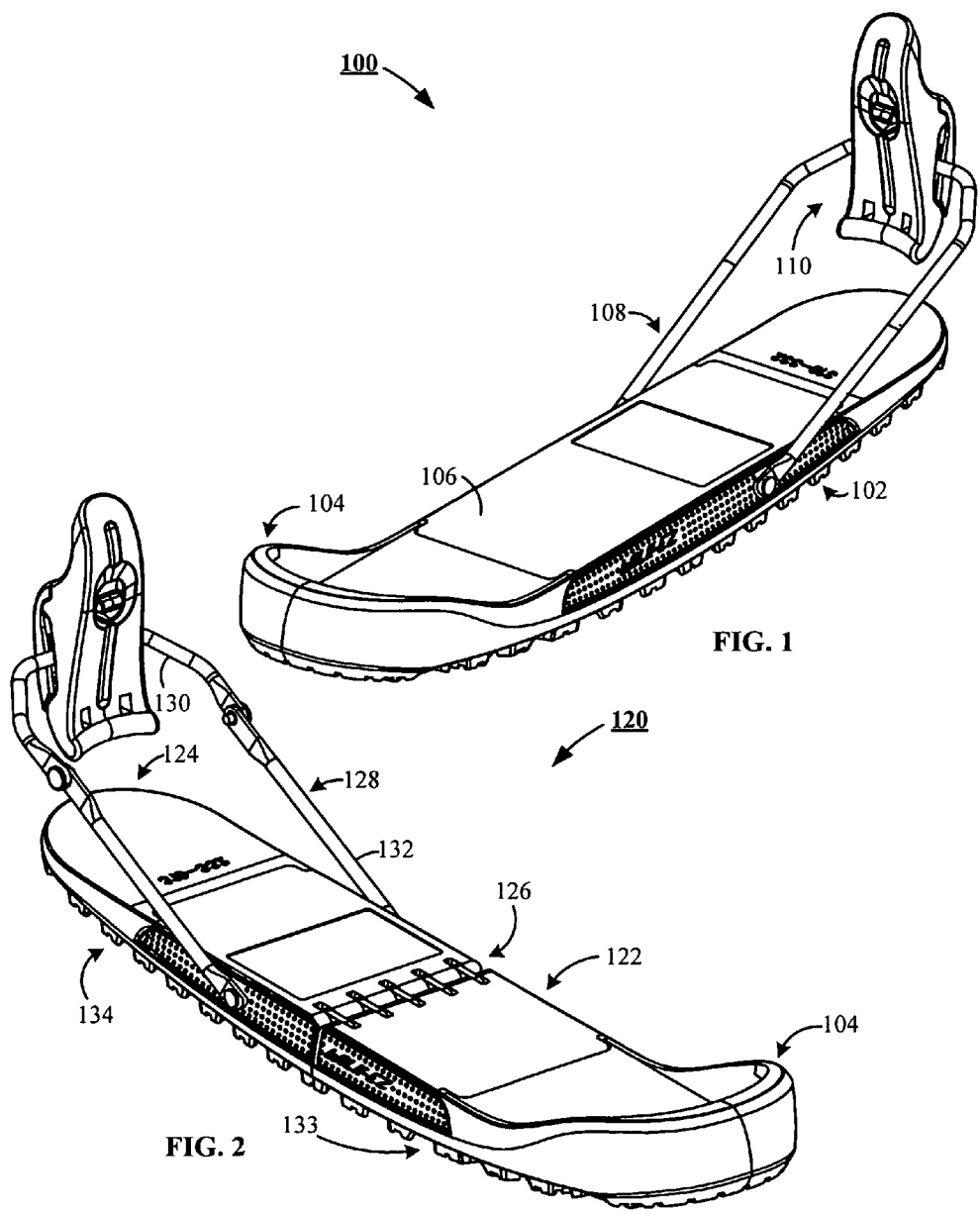
FIG. 1 shows a top perspective view of an embodiment of an inventive detachable sole.
FIG. 2 shows a top perspective view of an alternate embodiment of the inventive detachable sole.

Referring to the drawings, FIG. 1 shows an inventive detachable sole 100 that includes a tread portion 102, which includes a toe confinement portion 104, attached to a chassis 106. In a preferred embodiment, the tread portion 102 is attached to the chassis 106 through the use of an overmold process. However, alternate techniques may be used for the attachment of the tread portion 102 to the chassis 106, such as through the employment of adhesive material, or by sonically welding the components together.

In a preferred embodiment, the chassis 106 is formed from glass filled polypropylene compound, in which the compound contains between 10-30% glass by volume, and preferably 20% glass by volume, and the tread portion 102 preferably formed from a quasi pliable polymer such as the thermoplastic elastimer resin (TPE), or a polyurethane.

FIG. 1 further shows the inventive detachable sole 100 further includes an attachment hoop 108, which is preferably formed from nickel plated steel, but may be formed from alternate materials such as a carbon filed compound, or stainless steel. In a preferred embodiment, the attachment hoop 108 supports a latch 110, that is preferably an over-center latch. The latch 110 accommodates attachment of the detachable sole 100 to a plurality of ankle and foot coverings.

Turning to FIG. 2, shown therein is an alternate preferred embodiment of the inventive detachable sole 120. In contrast to the detachable sole 100 (of FIG. 1), the detachable sole 120 includes a first sole portion 122 and a second sole portion 124 secured together by a hinge portion 126. Additionally, the attachment hoop 108 (of FIG. 1) of the detachable sole 100 differs from an attachment hoop 128 of the inventive detachable sole 120. The attachment hoop 128 provides two portions, a latch attachment portion 130 and a heel chassis attachment portion 132 hinged to the latch attachment portion 130. It is noted however that the inventive detachable sole 120 and the inventive detachable sole 100 share the latch 110 in common.

Figure 3:
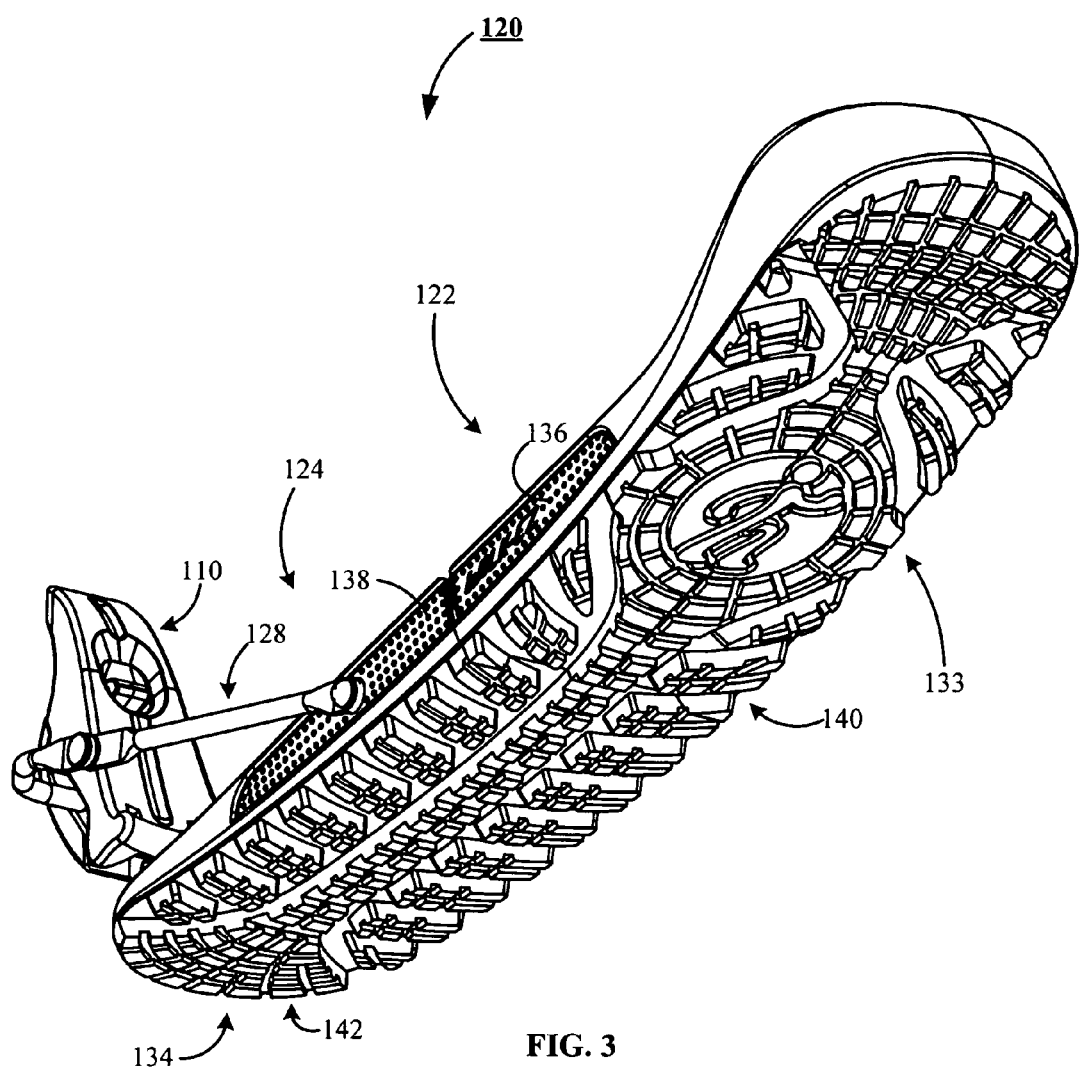
FIG. 3 is a bottom perspective view of tread portions of the inventive detachable sole of FIG. 2.

FIG. 3 shows the first sole portion 122 includes a toe tread portion 133, and the second sole portion 124 includes a heel tread portion 134. As with the tread portion 102 (of FIG. 1), the toe and heel tread portions 133,134 are preferably attached through the use of an overmold process. FIG. 3 further shows that the first sole portion 122 includes a side cap 136, and the second sole portion 124 includes a side cap 138. It will be understood that a tread pattern 140 of the toe tread portion 133, and a tread pattern 142 of the heel tread portion 134 represent preferred tread patterns, and do not impose limitations on the present invention. Those skilled in the art understand that alternate tread patterns may be utilized, and slip resistance mechanisms such as studs (similar to studs used on studded snow tires) may be incorporated within tread patterns 140 and 142, which fall within the scope of the present invention.

Figure 4:
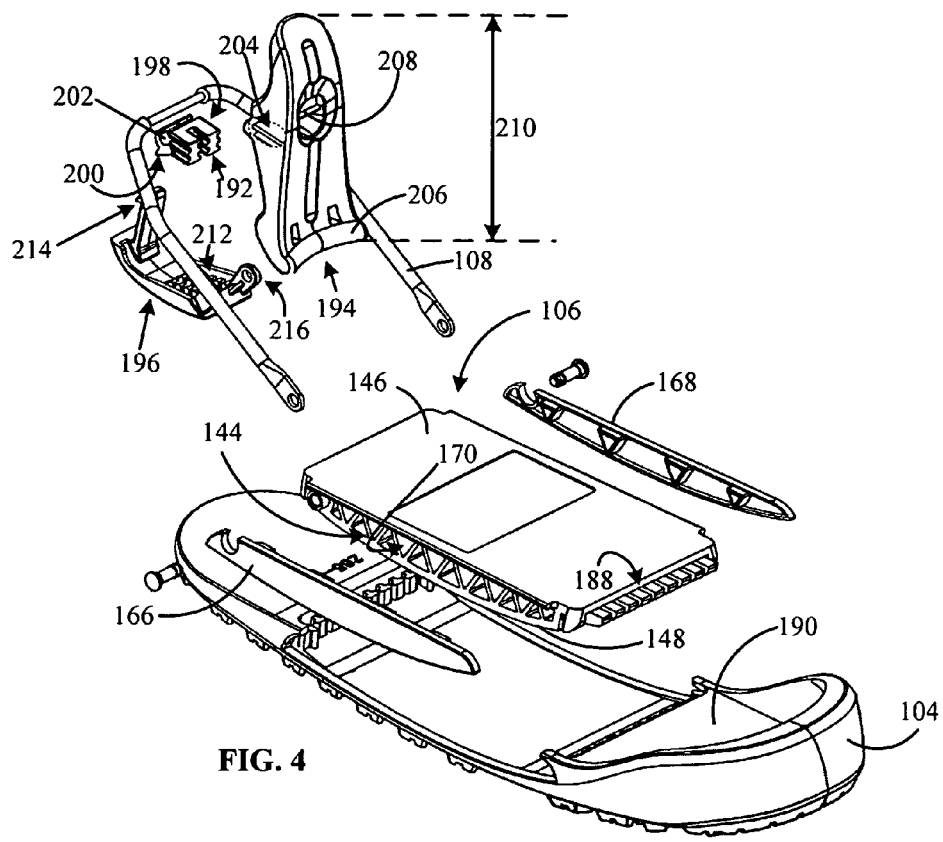
FIG. 4 is an exploded perspective view of the inventive detachable sole of FIG. 1.
Figure 5:
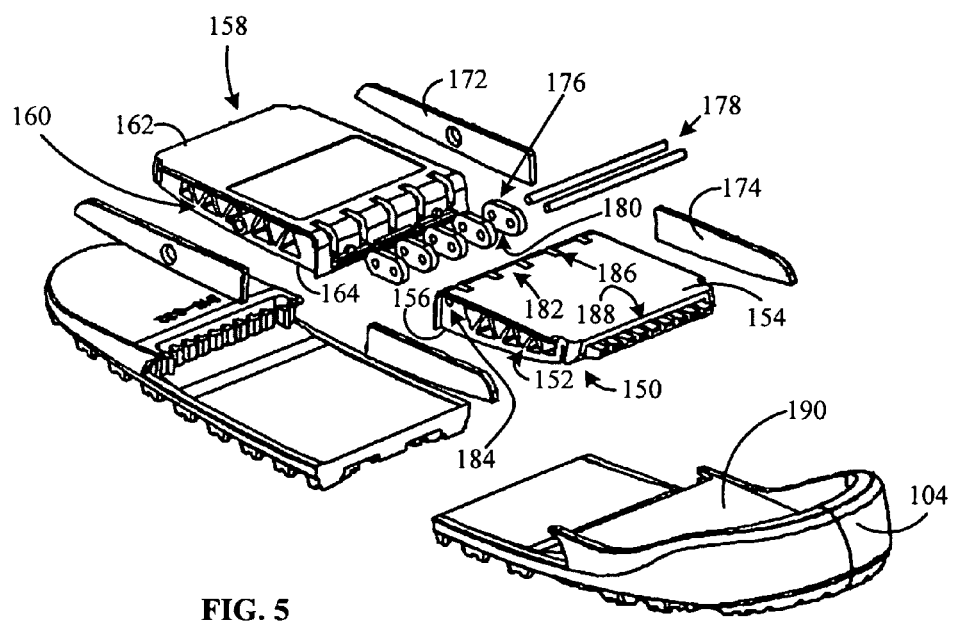
FIG. 5 is an exploded perspective view of the inventive detachable sole of FIG. 2.

The exploded perspective views of the inventive detachable soles 100 and 120 of FIG. 4 and FIG. 5 respectively may be best viewed in concert to provide an enhanced understanding of the commonalities and differences between the inventive detachable soles 100 and 120.

FIG. 4 shows chassis 106 includes a baffled support matrix 144 interposed between a top chassis portion 146 and a bottom chassis portion 148. FIG. 5 shows that the first sole portion 122 includes a toe chassis portion 150 constructed with a baffled support matrix 152 interposed between a top chassis portion 154 and a bottom chassis portion 156. The second sole portion 124 includes a heel chassis portion 158 constructed with a baffled support matrix 160 interposed between a top chassis portion 162 and a bottom chassis portion 164.

FIG. 4 shows the inventive detachable sole 100 includes a right side cap 166 and a left side cap 168. When the side caps 166 and 168 are attached to the baffled support matrix 144, debris is prevented from entering a plurality of cavities 170. It is noted that the plurality of cavities 170 collectively form the baffling members of the baffled support matrix 144. In addition to the side caps 136 and 138 (of FIG. 3), FIG. 5 further shows the inventive detachable sole 120 includes a pair of the left side caps 172 and 174, which are provided to preclude entry of debris into the baffled support matrix 152.

The hinge portion 126, as shown by FIG. 5, includes a plurality of hinge knuckles 176, and a pair of hinge pins 178. Each hinge knuckle 176 provides a pair of hinge pin apertures 180, and each hinge pin 178 is configured for sliding engagement within the hinge pin apertures 180. To accommodate each hinge knuckle 176, the toe chassis portion 150, and the heel chassis portion 158 each provide a plurality of hinge pin confinement portions 182, wherein each hinge pin confinement portions provides a passageway 184 sized to snugly accommodate each hinge pin 178 in mating contact. Interposed between each hinge pin confinement portions 182 are hinge knuckle reception cavities 186. Each hinge knuckle reception cavities 186 of the toe chassis portion 150 is positioned to align directly across from a corresponding hinge knuckle reception cavity 186 of the heel chassis portion 158.

When each the toe and heel chassis portions, 150,158 are outlined for mating with the hinge portion 126, each of the plurality of hinge knuckles are deposited within the hinge knuckle reception cavities 186, and each hinge pin is encouraged through the respective passageways 184 of the toe and heel chassis portions 150, 158 to combine the first sole portion 122 with the second sole portion 124 to form the inventive detachable sole 120.

As can be seen in FIG. 4, the chassis 106 includes a plurality of overmold interface cavities 188, which have been found useful in enhancing an ability of the tread portion 102 to adhere to the chassis 106. Preferably, during an overmold process, a selected polymer used in forming the tread portion 102 is forced through each of the overmold interface cavities 188, and reflowed together to form a continuous surface 190 adjacent to top chassis portion 146. The continuous surface 190 provides a bridge-way between the chassis 106 and the toe confinement portion 104. A quasi pliable polymer such as the thermoplastic elastimer resin (TPE), or a polyurethane is preferable for use in forming the tread portion 102, the continuous surface 190, and the toe confinement portion 104 because the selection of a quasi pliable polymer accommodates various toe configurations of a mating ankle and foot covering, such as a ski boot 220 (of FIG. 7). In a preferred embodiment, the quasi pliable polymer continuous surface 190, and the toe confinement portion 104 have been found useful in holding the inventive detachable sole 120 under tension when attached to the ski boot 220. However, as those skilled in the art will recognize, alternate methods of providing a tensile load to the detachable sole 120 to aid in maintaining a snug fit between the ski boot 220 and the inventive detachable sole 120 may be provided, without deviation from the scope and spirit of the present invention, for example, through use of a spring configuration.

The latch 110 of FIG. 4, which in a preferred embodiment is an over-center latch 110 that includes three primary components: a latch block 192, a latch body 194, and a latch door 196. The latch block 192 provides a latch body engagement feature 198, a latch door engagement feature 200, and an attachment hoop attachment feature 202. The latch body 194 provides a plurality of tension adjustment members 204 (one shown in cutaway view), an over-center pivot feature 206, and a catch receptacle 208.

In a preferred embodiment, the latch body engagement feature 198 of the latch block 192 is slid into engagement with a selected one of the plurality of tension adjustment members 204. Because the plurality of tension adjustment members 204 extend along a length 210 of the latch body 194, the selection of a specific tension adjustment member 204 determines a holding force imparted by the attachment hoop 108 on the chassis 106, which determines how tightly the inventive detachable sole 100 is secured adjacent a mating ankle and foot covering, such as orthopedic device 218 (of FIG. 6).

The latch door 196 is configured for engagement with the latch block 192 and the latch body 194. The latch body provides a plurality of latch block support channels 212, a latch door catch 214, and a pivot detent 216. Once the selection has been made for the particular tension adjustment member 204, and the latch body engagement feature 198 has been slid onto the selected tension adjustment member 204, a position of the latch block 192 relative to the catch receptacle 208 can be determined. When the relative position of the latch block 192 to the catch receptacle 208 has been determined, a specific latch block support channel 212 is selected by rotating the latch door catch 214 about the pivot detent 216 to engage the latch door engagement feature 200 with the catch receptacle 208. Once positioned, the latch door 196 mitigates a buildup of ice and snow around the interface of the latch body engagement feature 198 and the selected tension adjustment member 204.

Figure 6:
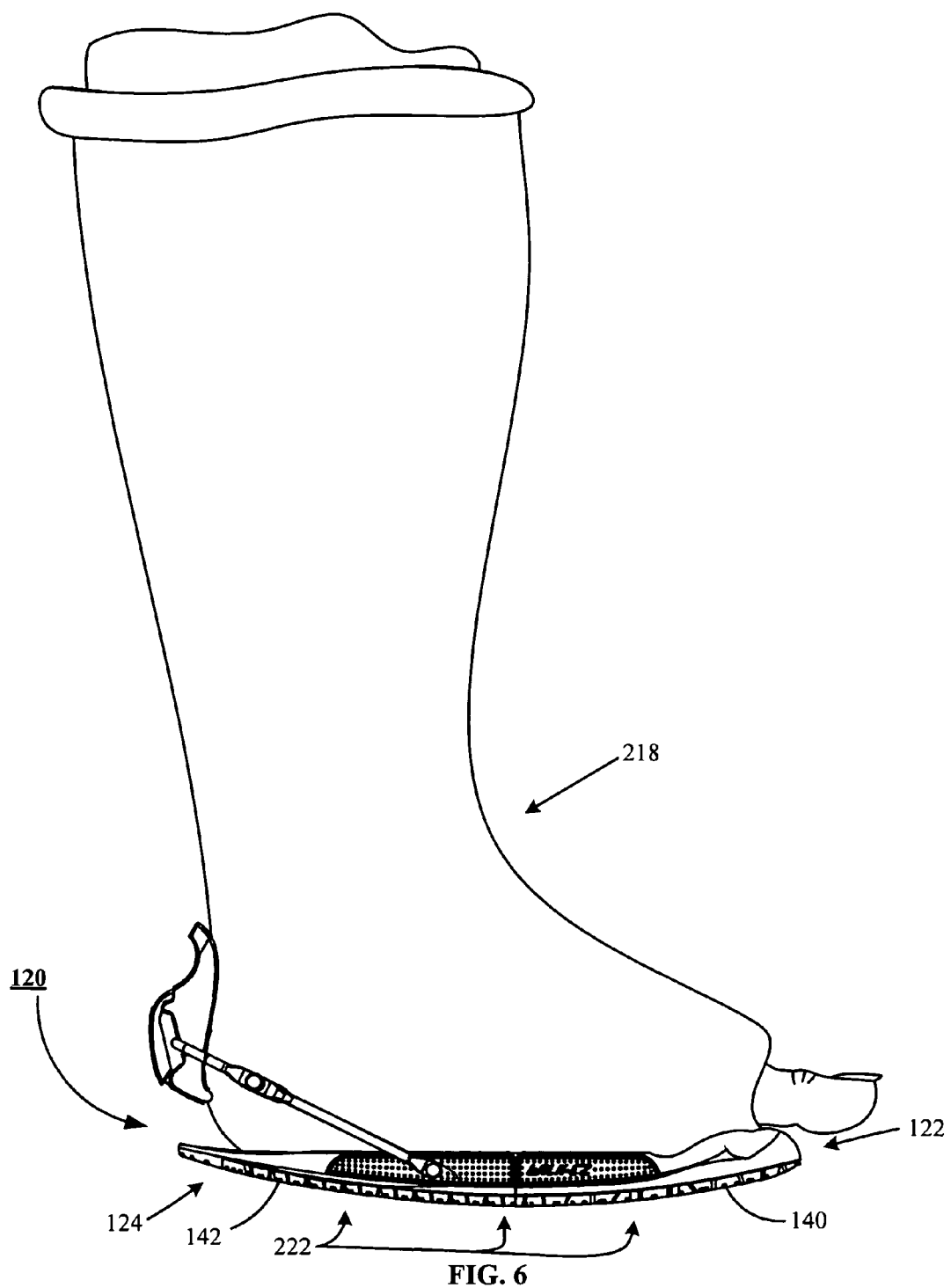
FIG. 6 shows a side elevational view of an alternative embodiment of the inventive detachable sole secure to an ankle and foot covering.
Figure 7:
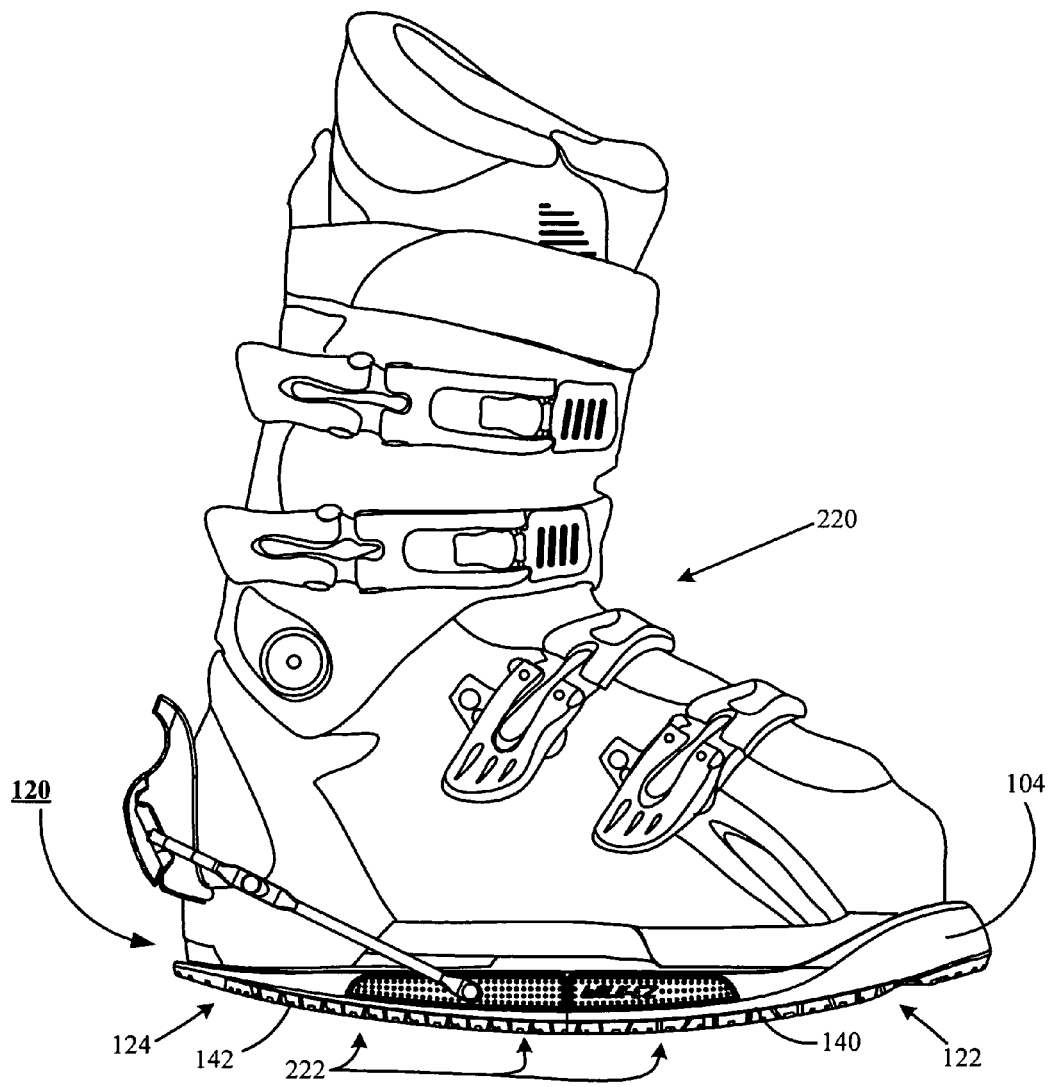
FIG. 7 illustrates a side elevational view of the inventive detachable sole of FIG. 2 secure to an alternate ankle and foot covering.

FIGS. 6 and 7 each show an example of a use for the inventive detachable sole 120. The applied use of the inventive detachable sole 120 depicted by FIG. 6 resides within the medical arts. The inventive detachable sole 120, provides an enhanced walking ability for an individual wearing an orthopedic device such as a cast 218. The enhanced walking ability provided for an individual wearing the cast 218 results from the concave shape 222 of the inventive detachable sole 120, and the preferred tread patterns 140 and 142, respectively of the first sole portion 122 and the second sole portion 124.

The applied use of the inventive detachable sole 120 depicted by FIG. 7 resides within the sports equipment arts. The inventive detachable sole 120, provides an enhanced walking ability for an individual wearing, for example an Alpine type ski boot, such as 220. The enhanced walking ability provided for an individual wearing the ski boot 220 results from the concave shape 222 of the inventive detachable sole 120, the preferred tread patterns 140 and 142, respectively of the first sole portion 122 and the second sole portion 124, the toe confinement portion 104, and the adjustability features of the over-center latch 110.

Figure 8:
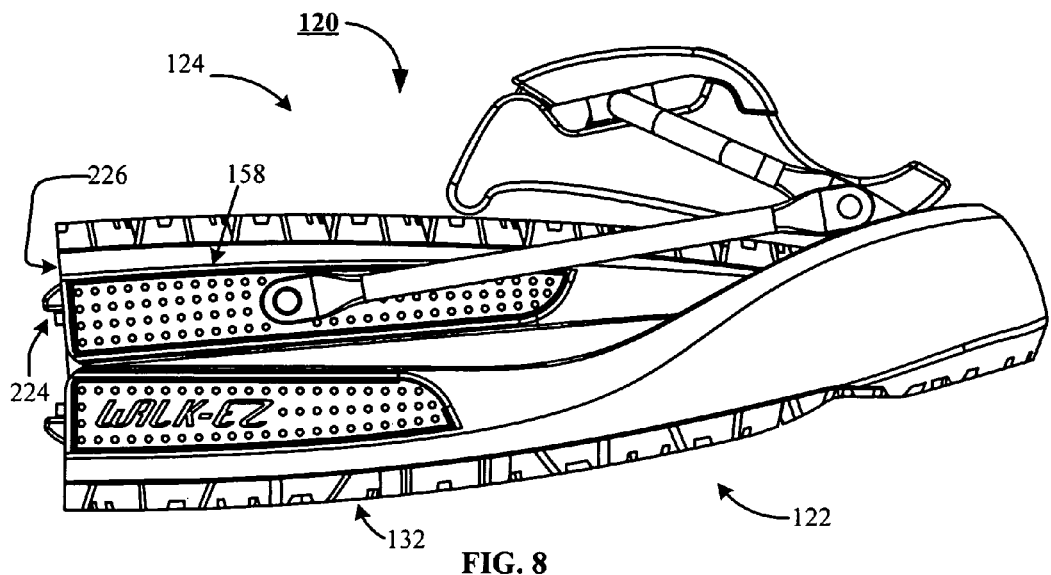
FIG. 8 is a side elevational view of the inventive detachable sole of FIG. 2 shown in a collapsed configuration ready for storage.
Figure 9:
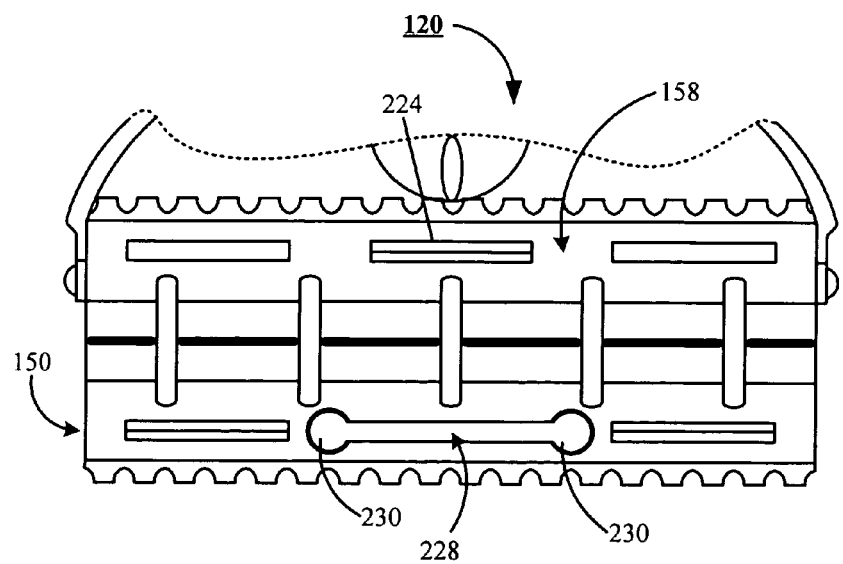
FIG. 9 is a rear elevational view of the inventive detachable sole of FIG. 2 shown in a collapsed configuration ready for storage.

FIG. 8 provides a best view of a chassis stabilization member 224, which extends from the proximal end 226 of the heel chassis portion 158, while FIG. 9 provides a best view of a chassis stabilization aperture 228. The chassis stabilization aperture 228 is configured to accommodate penetration of the chassis stabilization member 224 when the heel chassis portion 158 is folded into alignment with the toe chassis portion 150. FIG. 9 further shows the inclusion of a pair of retention stud apertures 230. The retention stud apertures 230 accommodate penetration of a pair of respective chassis retention studs 232 of FIGS. 10 and 11.

It will be noted that FIG. 8 shows the inventive detachable sole 120 to be in a partially folded position. It will be understood that the depiction of the inventive detachable sole 120 in a partially folded position was provided to enhance an understanding of the present invention and does not impose any limitations on the present invention. In a preferred embodiment, in a fully folded position, the first sole portion 122 aligns with the second sole portion 124 in a substantially flat continuous manner.

Turning to FIGS. 10 and 11, a left side elevational view of a storage rack 234 is provided by FIG. 10, and a right side elevational view of the storage rack 234 is provided by FIG. 11. The storage rack 234 includes a main body portion 236 with a concave surface 238, configured for mating conformance with the toe tread portion 133 (of FIG. 8). A hook adjustment portion 240 projects from a proximal end 242 of the main body portion 236. The hook adjustment portion 240 supports and accommodates a hook attachment member 244. The hook attachment member 244 is useful for attachment of the inventive detachable sole 120 to an ankle and foot covering such as the ski boot 220 of FIG. 7.

In a preferred embodiment, the hook adjustment portion 240 provides for an adjustment, in a vertical direction (as shown by FIG. 11), of the hook attachment member 244 to accommodate varying sizes of ski boots, or orthopedic devices. The storage rack 234 further includes a chassis support shelf 246 extending from a proximal end 247 of the main body portion 236. The chassis support shelf 246 provides a support member for the chassis retention studs 232. The chassis retention studs 232 interact with the retention stud apertures 230 (of FIG. 9) to position the toe tread portion 133 adjacent the main body portion 236. FIG. 11 further shows a main body support 248 extending from a mid-portion 250 of the main body portion 236.

FIG. 11 further shows a strap support member 252 projecting from the proximal end 242 of the main body portion 236. A garment confinement slot 254 is formed between the hook adjustment portion 240 and said strap support member 252. With the inventive detachable sole 120 attached to a ski boot, such as ski boot 220 (of FIG. 7), the garment confinement slot 254 accommodates placement of a garment portion, such as a pant leg of the pair of ski pants (not shown). To secure the inventive detachable sole 120 to the ski boot 220 (as shown in FIG. 7), a strap pin 256 is attached to a distal end 258 of the strap support member 252, and a strap 260 attached to the strap pin 256. The strap 260 interacts with the over-center latch 110 to confine the toe tread portion 133 adjacent the main body portion 236.

FIG. 12 is provided to enhance an understanding of a preferred configuration of the hook attachment member 244 relative to the hook adjustment portion 240. In a preferred embodiment the hook attachment member 244 is formed from stainless spring steel, however those skilled in the art will understand that alternate materials and configurations may provide substitute design choices for the hook attachment member 244, and still remain within the scope and spirit of the present intention.

Figure 13:
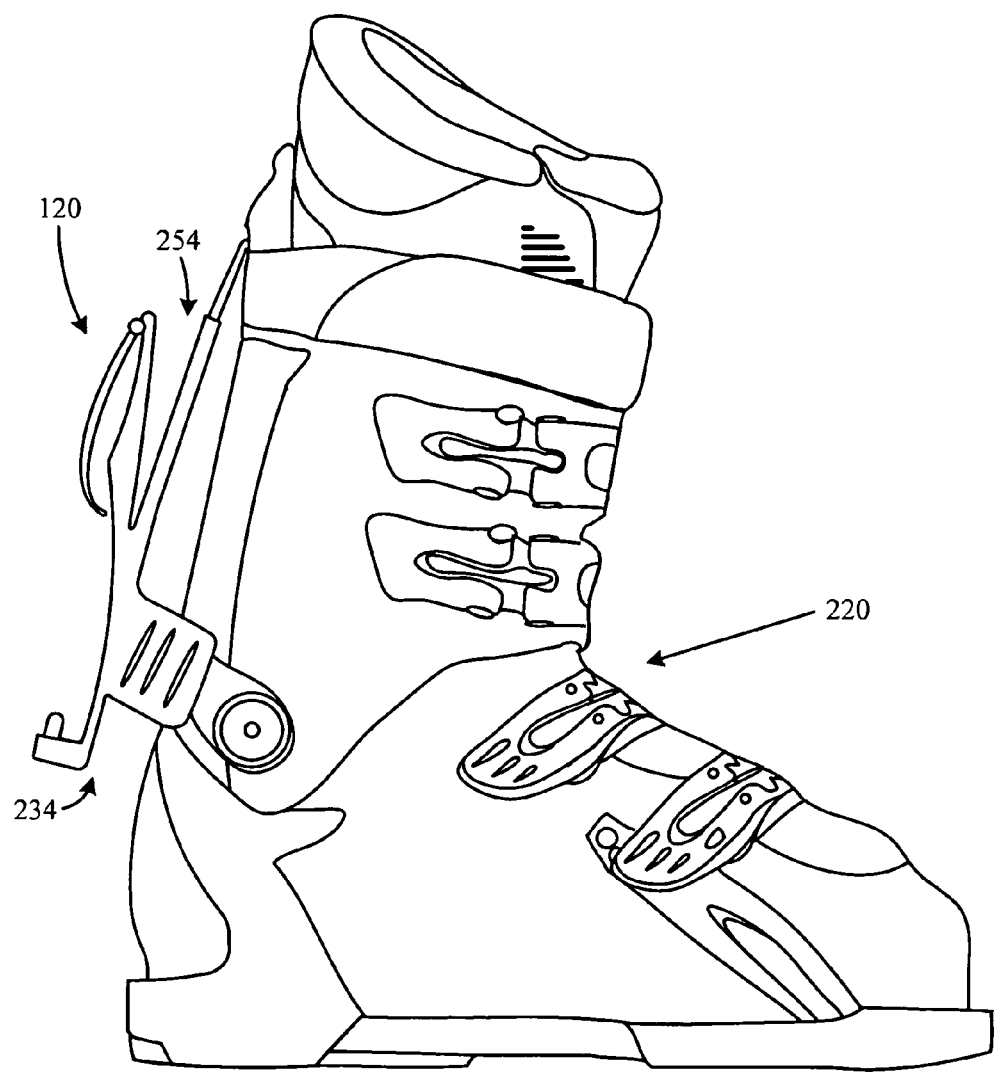
FIG. 13 is a side elevational view of the inventive detachable sole storage rack of FIG. 10 attached to the alternate ankle and foot covering of FIG. 7.
Figure 14:
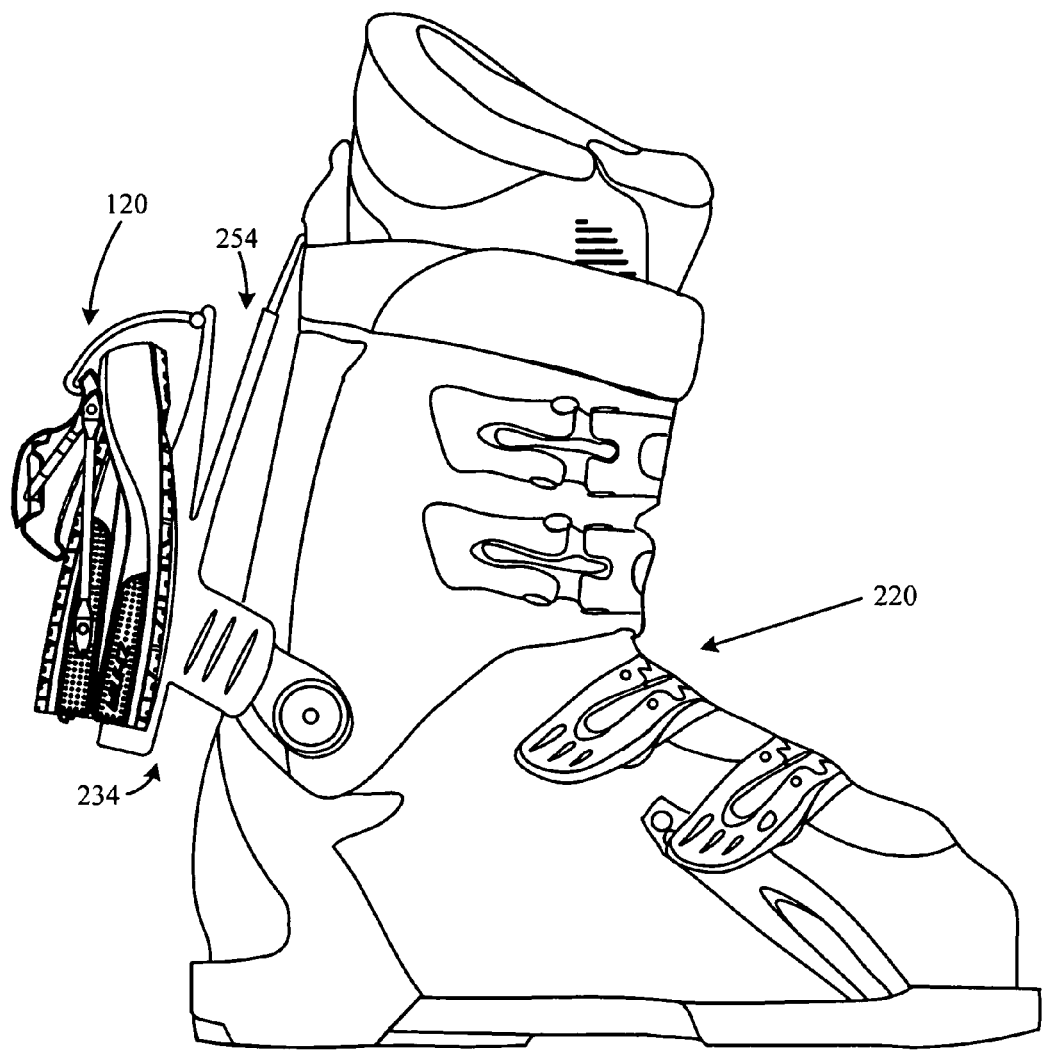
FIG. 14 is a side elevational view of the inventive combination of the present invention.

FIG. 13 provides an elevational view of a preferred embodiment configuration of the storage rack 234 attached to ski boot 220, while FIG. 14 serves to shows the configuration of FIG. 13 with the addition of the inventive detachable sole 120 of the present invention. By viewing FIG. 14 it will be noted that the storage rack 234, when attached to the ski boot 220, provides for convenient storage of the inventive detachable sole 120, when the inventive detachable sole 120 is detached from the ski boot 220, for example during periods of time in which an individual is engaged in skiing down a slope.

Figure 15:
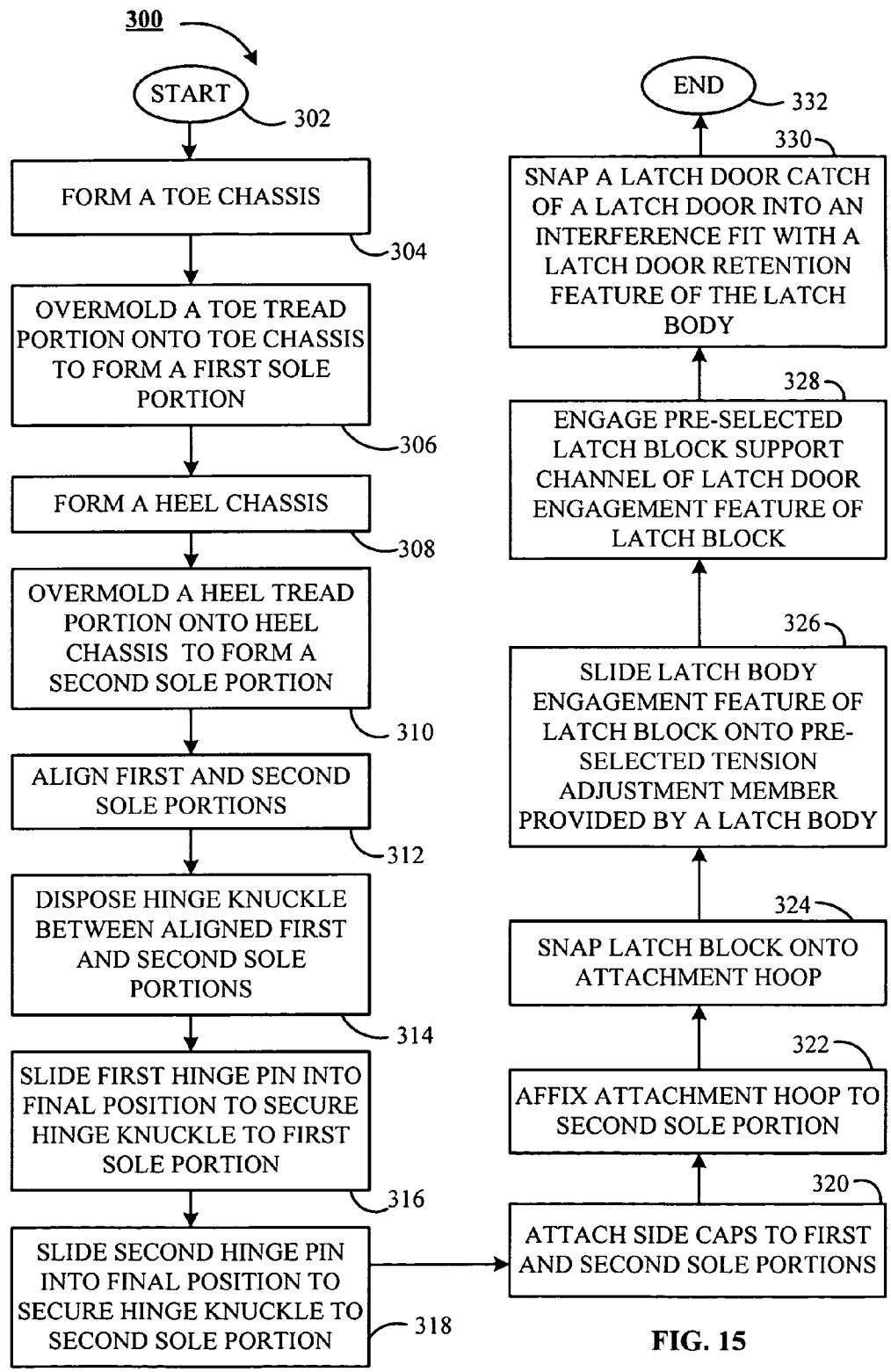
FIG. 15 is a flow diagram of the method of making the inventive detachable sole of FIG. 2.

Flowchart 300 of FIG. 15 shows method steps of a process of making an inventive detachable sole (such as 120). The process commences at start step 302 and continues at process step 304. At process step 304, a toe chassis portion (such as 150) is formed, and at process step 306 a toe tread portion (such as 133) is overmolded onto the toe chassis. At process step 308, a heel chassis (such as 158) is formed and at process step 310 a heel tread portion (such as 134) is overmolded onto the heel chassis.

At process step 312, a first sole portion (such as 122) is aligned to a second sole portion (such as 124). With the first and second sole portions aligned, at process step 314, a process of installing a hinge portion (such as 126) is commenced by disposing each of a plurality of hinge knuckles (such as 176) within corresponding knuckle reception cavities (such as 186). At process step 316, a first of a pair of hinge pins (such as 178) is slid into its final position to secure the hinge knuckle to the first sole portion, and at process step 318 the second of the pair of hinge pins is slid into position to secure the hinge knuckle to the second sole portion.

At process step 320, side caps (such as 136, 138, 172, and 174) are attached to each of the first and second sole portions. The attachment of the side caps mitigates encroachment of debris from migrating into each of the plurality of cavities (such as 170), which collectively form baffling members of a baffled support matrix (such as 144). At process step 322, an attachment hoop (such as 128) is attached to the second sole portion, and at process step 324 a latch block (such as 192) is snapped onto the attachment hoop.

At process step 326, a latch body engagement feature (such as 198), is slid onto a pre-selected tension adjustment member (such as 204), provided by a latch body (such as 194). At process step 328, a pre-selected latch body support channel (such as 212) of a latch door (such as 196) engages a latch door engagement feature (such as 200) of the latch block. At process step 330, a latch door catch (such as 214) is snapped into an interference fit with a catch receptacle (such as 208) of the latch body, and the process concludes at end process step 332.

Figure 16:
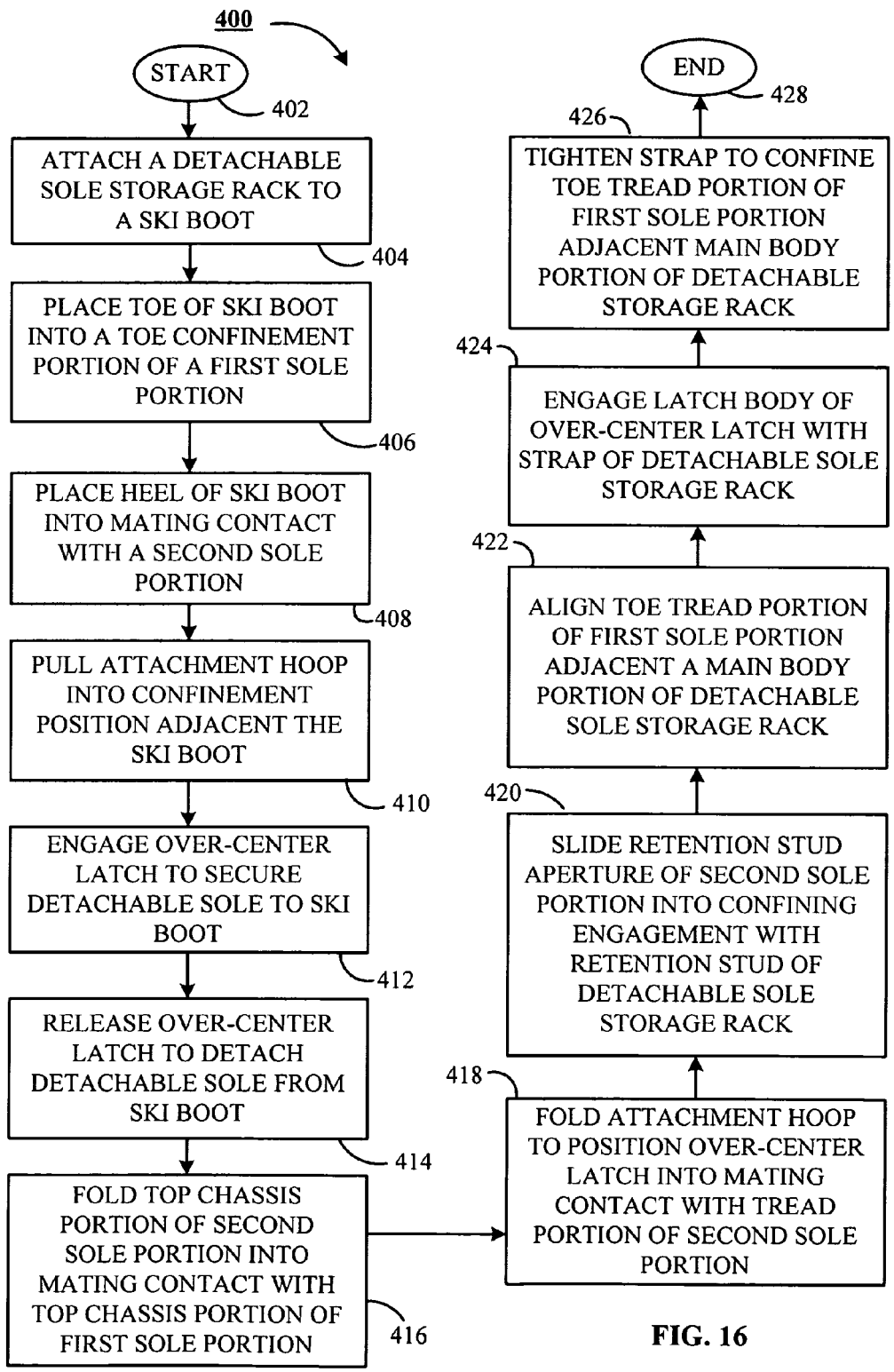
FIG. 16 is flow diagram of a method of using the inventive combination of FIG. 14.

Flowchart 400 of FIG. 16 shows method steps of a process of using an inventive detachable sole (such as 120). The process commences at start step 402 and continues at process step 404. At process step 404, a detachable sole storage rack (such as 234), is attached to a ski boot (such as 220). At process step 406, a toe of a ski boot is placed into a toe confinement portion (such as 104) of a first sole portion (such as 122). At process 408, a heel of the ski boot is placed in mating contact with a second sole portion (such as 124). At process step 410, an attachment hoop (such as 128) is pulled into a confinement position adjacent the ski boot, and at process step 412 an over-center latch (such as 110) is engaged to secure the detachable sole to the ski boot.

At process step 414, the over-center latch is released to detach the detachable sole from the ski boot. At process step 416, a top chassis portion (such as 162) of the second sole portion is folded into mating contact with a top chassis portion (such as 154) of the first sole portion. At process step 418, the attachment hoop is folded to position the over-center latch into mating contact with a heel tread portion (such as 134) of the second sole portion. At process step 420, a pair of retention stud apertures (such as 230), are slid into confining engagement with a pair of chassis retention studs (such as 232). At process step 422, a toe tread portion (such as 133) of the first sole portion is aligned adjacent a main body portion (such as 236) of the detachable sole storage rack.

A latch body (such as 194) of the over-center latch is lashed with a strap (such as 260) to the detachable storage rack at process step 424. At process step 426, the strap is tightened to confine the toe tread portion of the first sole portion adjacent the main body portion of the detachable storage rack and the process concludes at end process step 428.

Figure 17:
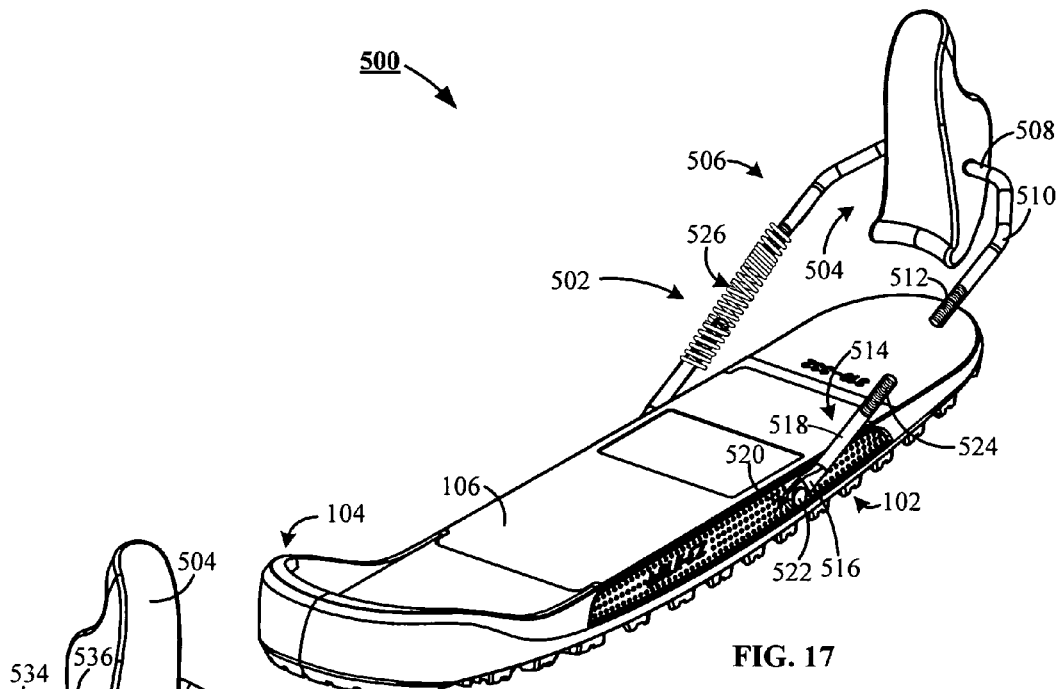
FIG. 17 shows a top perspective view of another alternate embodiment of an inventive detachable sole.

FIG. 17 shows another alternate embodiment of the inventive detachable sole 500 that includes a latch assembly 502 secured to the baffled support matrix 152 of FIG. 4, and supporting a catch 504. The detachable sole 500 further includes at least a tread portion 102, which includes a toe confinement portion 104, attached to a chassis 106. In a preferred embodiment, the tread portion 102 is attached to the chassis 106 through the use of an overmold process. However, alternate techniques may be used for the attachment of the tread portion 102 to the chassis 106, such as through the employment of adhesive material, or by sonically welding the components together.

In a preferred embodiment, the chassis 106 is formed from a glass filled polypropylene compound, in which the compound contains between 10-30% glass by volume, and preferably 20% glass by volume, and the tread portion 102 preferably formed from a quasi pliable polymer such as the thermoplastic elastimer resin (TPE), or a polyurethane.

The latch assembly 502 provides a catch support 506 supporting the catch 504 (of FIG. 17). The catch support 506 provides a catch mount portion 508, upon which the catch 504 resides, and an alignment portion 510 projecting from the catch mount portion 508. The catch alignment portion 510 provides a first threaded portion 512, which preferably presents a left-handed thread.

The latch assembly 502 preferably further includes, a chassis attachment member 514 that includes a chassis mount portion 516 and an extension portion 518. The chassis mount portion 516 provides an attachment aperture 520 (not separately shown) that accommodates passage of a fastener 522, which secures the extension portion to the chassis 106. The extension portion 518 preferably provides a second threaded portion 524, which preferably presents a left-handed thread.

In a preferred embodiment, the left-hand thread presentation of the first threaded portion 512 is secured to the left-hand thread presentation of the second threaded portion 524 by an adjustment member 526. Preferably, the adjustment member is formed from a stainless steel coiled spring; however, those skilled in the art will understand that alternate configurations and materials may be substituted for the preferred stainless steel coiled spring, without deviating from the scope of the present invention.

In a preferred embodiment, the preferred stainless steel coiled spring is a right-hand wound coil spring, and both the first and second threaded portions, 512 and 524, present left-hand female threads. The continuous coil body of the right-hand wound coil spring (having an inner diameter corresponding to the thread depth of the left-hand female threads of the first and second threaded portions, 512 and 524) forms a corresponding mating and continuous left-hand male thread. Accordingly, by rotating the right-hand coil spring counter-clockwise, the continuous coil body of the right-hand wound coil spring settles in, and adjusts itself to the pitch of the left-hand female threads of the first and second threaded portions, 512 and 524, and travels along the length of the corresponding first and second threaded portions, 512 and 524.

Figure 18:
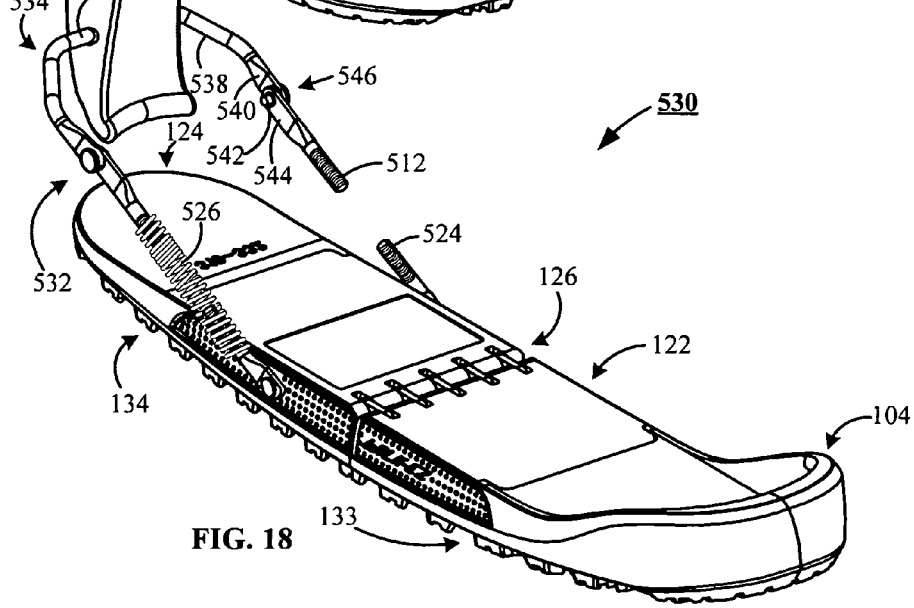
FIG. 18 shows a top perspective view of another alternative embodiment of an inventive detachable sole.

Turning to FIG. 18, shown therein is another alternate preferred embodiment of an inventive detachable sole 530. In contrast to the detachable sole 500 (of FIG. 17), the detachable sole 530 includes a first sole portion 122 and a second sole portion 124, secured together by a hinge portion 126. Additionally, a latch assembly 532 of the inventive detachable sole 530, differs from the latch assembly 502 of the inventive detachable sole 500 (of FIG. 17), through an inclusion of a hinge 546.

Preferably, the latch assembly 532 provides a catch support 534 that provides a catch mount portion 536, upon which the catch 504 resides, and an alignment portion 538 projecting from the catch mount portion 508. The catch alignment portion 538 provides: a first hinge member 540; a hinge pin 542; and a second hinge member 544, which form the hinge 546. The alignment portion 538 also preferably includes the first threaded portion 512, which preferably presents a left-handed thread.

Figure 19:
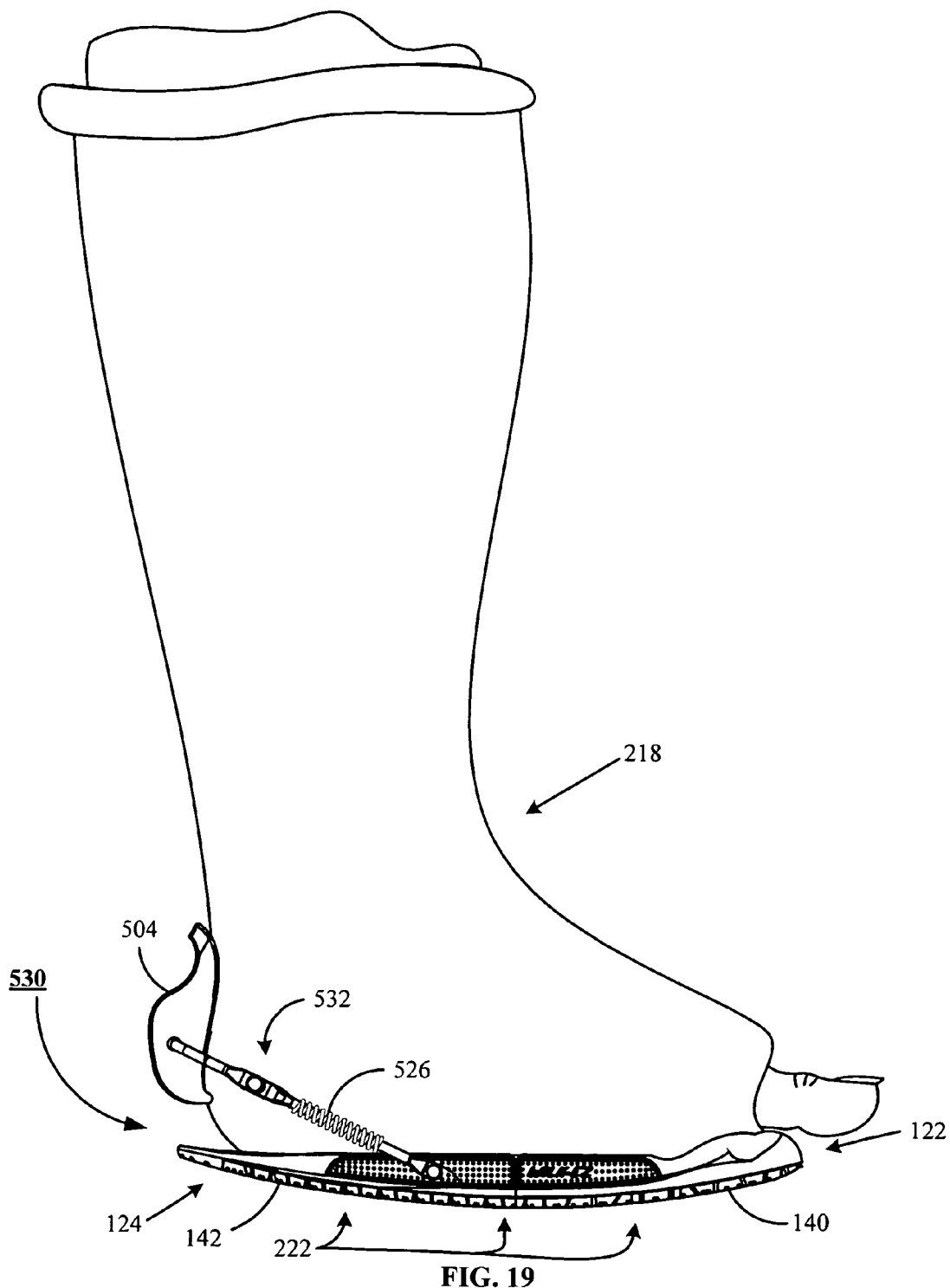
FIG. 19 shows a side elevational view of an alternate alternative embodiment of the inventive detachable sole secured to an ankle and foot covering.
Figure 20:
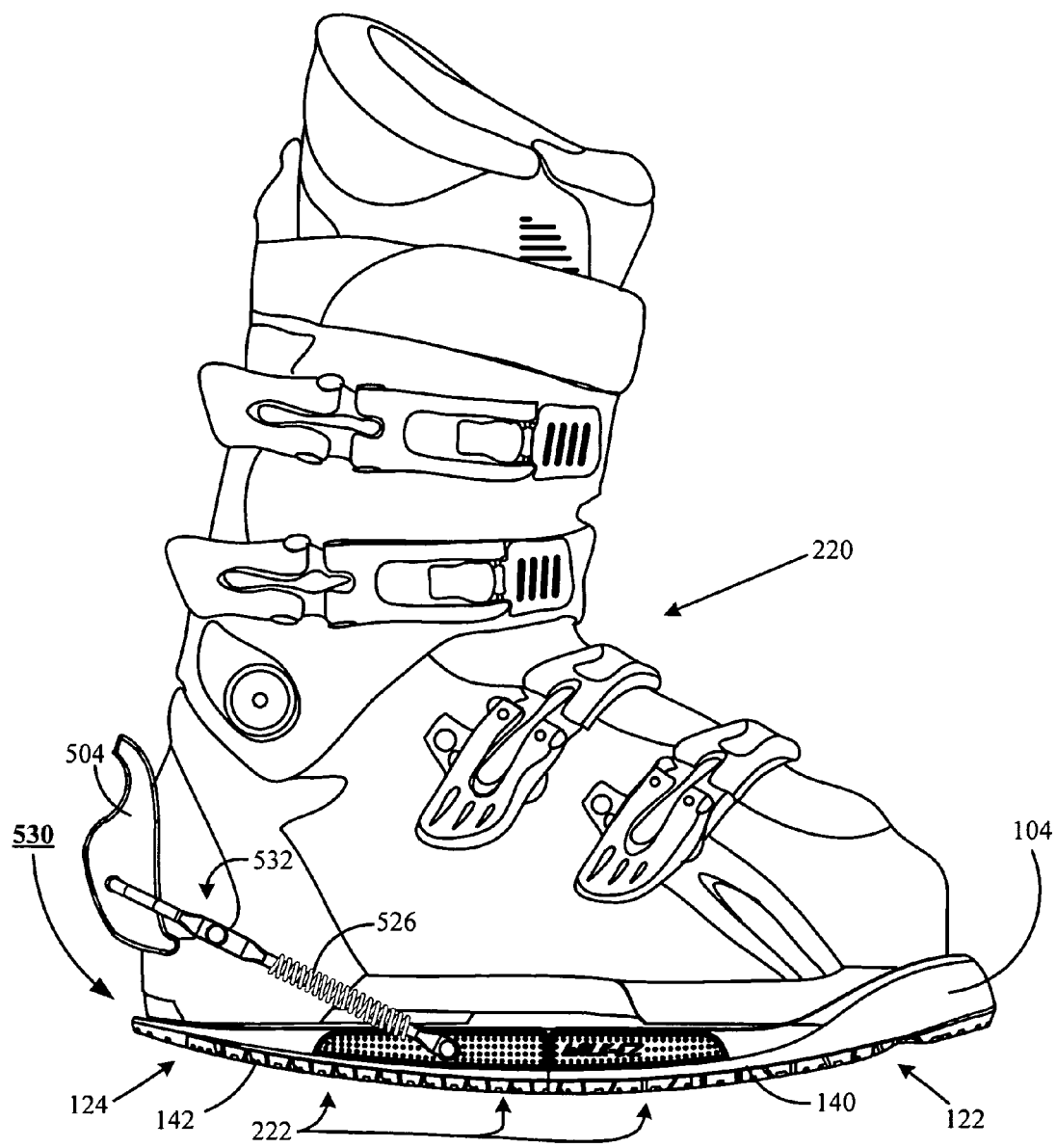
FIG. 20 illustrates a side elevational view of the inventive detachable sole of FIG. 18 secured to an alternate ankle and foot covering.

FIGS. 19 and 20 each show an example of a use for the inventive detachable sole 530. The applied use of the inventive detachable sole 530 depicted by FIG. 19 resides within the medical arts. The inventive detachable sole 530, provides an enhanced walking ability for an individual wearing an orthopedic device such as a cast 218. The enhanced walking ability provided for an individual wearing the cast 218 results from the concave shape 222 of the inventive detachable sole 530, and the preferred tread patterns 140 and 142, respectively of the first sole portion 122 and the second sole portion 124.

The applied use of the inventive detachable sole 530 depicted by FIG. 20 resides within the sports equipment arts. The inventive detachable sole 530, provides an enhanced walking ability for an individual wearing, for example, an Alpine type ski boot, such as 220. The enhanced walking ability provided for an individual wearing the ski boot 220 results from the concave shape 222 of the inventive detachable sole 120, the preferred tread patterns 140 and 142, respectively of the first sole portion 122 and the second sole portion 124, the toe confinement portion 104, and the adjustability features of the latch assembly 532.

Figure 21:
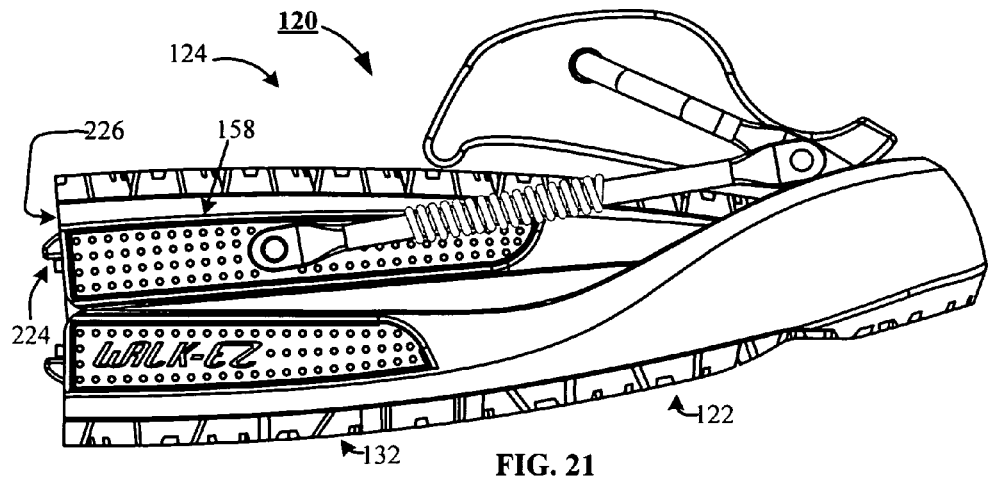
FIG. 21 is a side elevational view of the inventive detachable sole of FIG. 18 shown in a collapsed configuration ready for storage.

It will be noted that FIG. 21, shows the inventive detachable sole 530 to be in a partially folded position. It will be understood that the depiction of the inventive detachable sole 530 in a partially folded position was provided to enhance an understanding of the present invention and does not impose any limitations on the present invention. In a preferred embodiment, in a fully folded position, the first sole portion 122 aligns with the second sole portion 124 in a substantially flat continuous manner.

Figure 22:
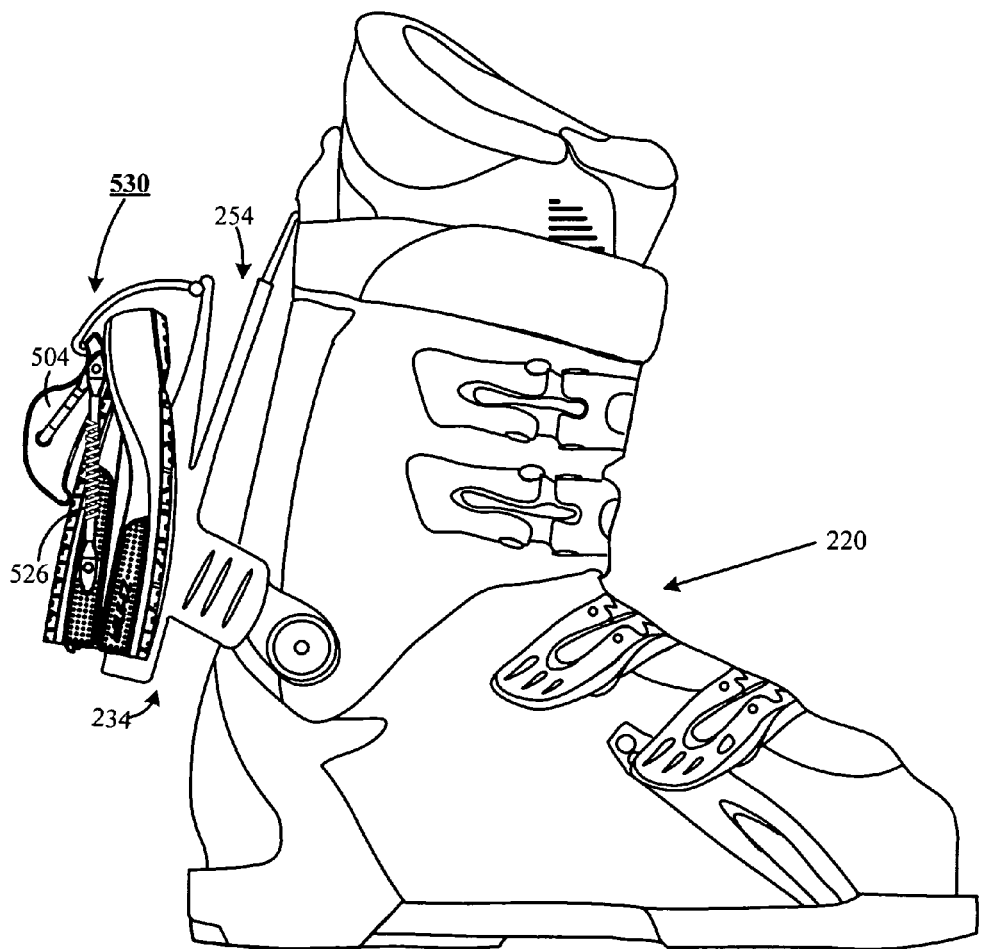
FIG. 22 is a side elevational view of an alternate inventive combination of the present invention.

FIG. 22 provides an elevational view of a preferred embodiment configuration of the storage rack 234 attached to the ski boot 220, and the inventive detachable sole 530 interacting with and confined by the storage rack 234. By viewing FIG. 22, it will be noted that the storage rack 234, when attached to the ski boot 220, provides for convenient storage of the inventive detachable sole 530, when the inventive detachable sole 530 is detached from the ski boot 220, for example, during periods of time in which an individual is engaged in skiing down a slope.

Figure 23:
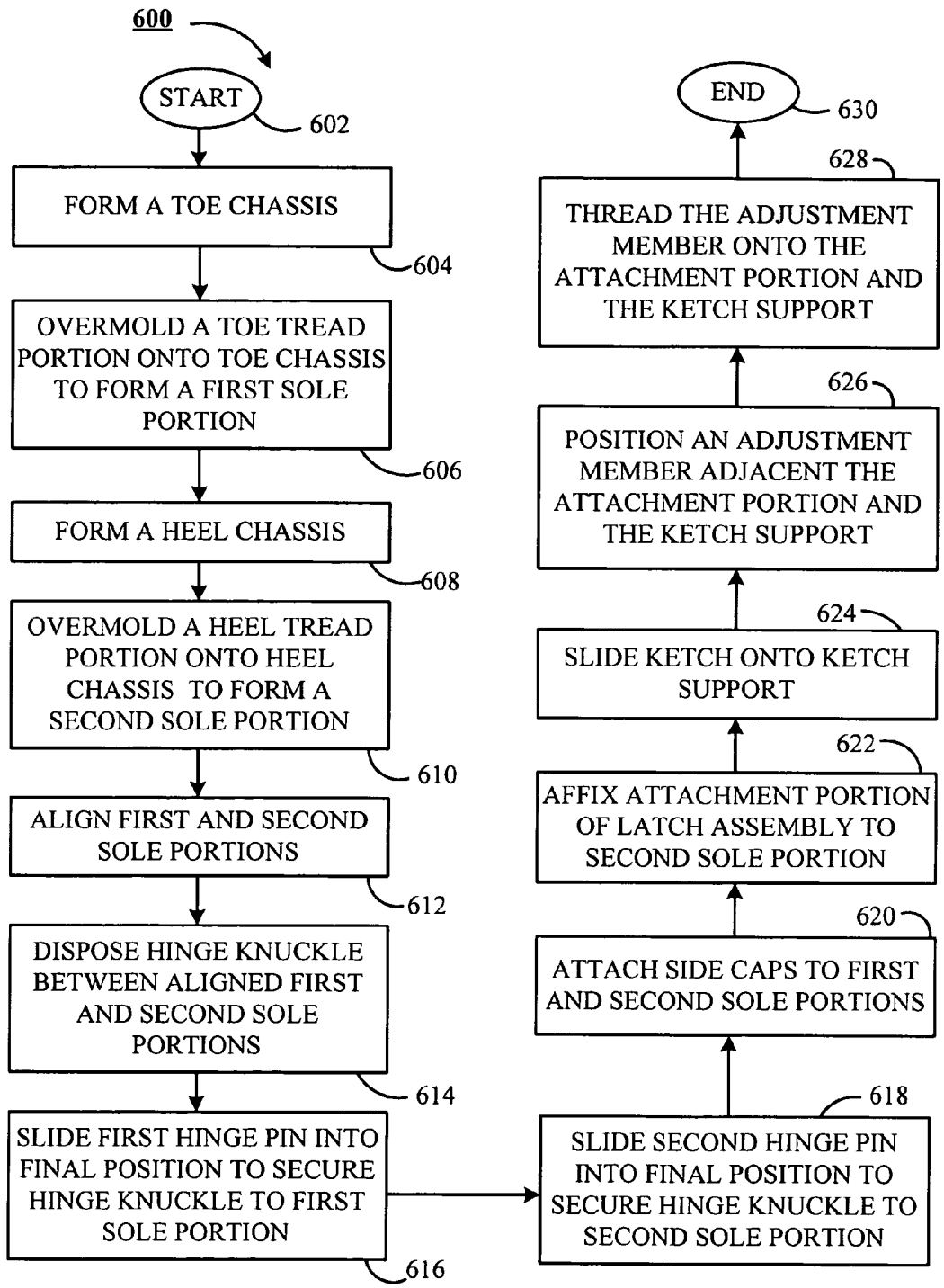
FIG. 23 is a flow diagram of the method of making the inventive detachable sole of FIG. 18.

Flowchart 600 of FIG. 23, shows method steps of a process of making an inventive detachable sole (such as 530). The process commences at process start step 602 and continues at process step 604. At process step 604, a toe chassis portion (such as 150) is formed, and at process step 606, a toe tread portion (such as 133) is overmolded onto the toe chassis. At process step 608, a heel chassis (such as 158) is formed, and at process step 610, a heel tread portion (such as 134) is overmolded onto the heel chassis.

At process step 612, a first sole portion (such as 122) is aligned to a second sole portion (such as 124). With the first and second sole portions aligned, at process step 614, a process of installing a hinge portion (such as 126) is commenced by disposing each of a plurality of hinge knuckles (such as 176) within corresponding knuckle reception cavities (such as 186). At process step 616, a first of a pair of hinge pins (such as 178) is slid into its final position to secure the hinge knuckle to the first sole portion, and at process step 618, the second of the pair of hinge pins is slid into position to secure the hinge knuckle to the second sole portion.

At process step 620, side caps (such as 136, 138, 172, and 174) are attached to each of the first and second sole portions. The attachment of the side caps mitigates encroachment of debris from migrating into each of the plurality of cavities (such as 170), which collectively form baffling members of a baffled support matrix (such as 144). At process step 622, an attachment portion (such as chassis attachment member 514) of a latch assembly (such as 532) is attached to the second sole portion, and at process step 624, a catch (such as 504) is slid onto a catch mount portion (such as 536) of a catch support (such as 534).

At process step 626, an adjustment member (such as 526) is positioned adjacent the attachment portion and the catch portion. At process step 628, the adjustment portion is threaded onto the attachment portion and the catch portion, and the process concludes at end process step 630.

Figure 24:
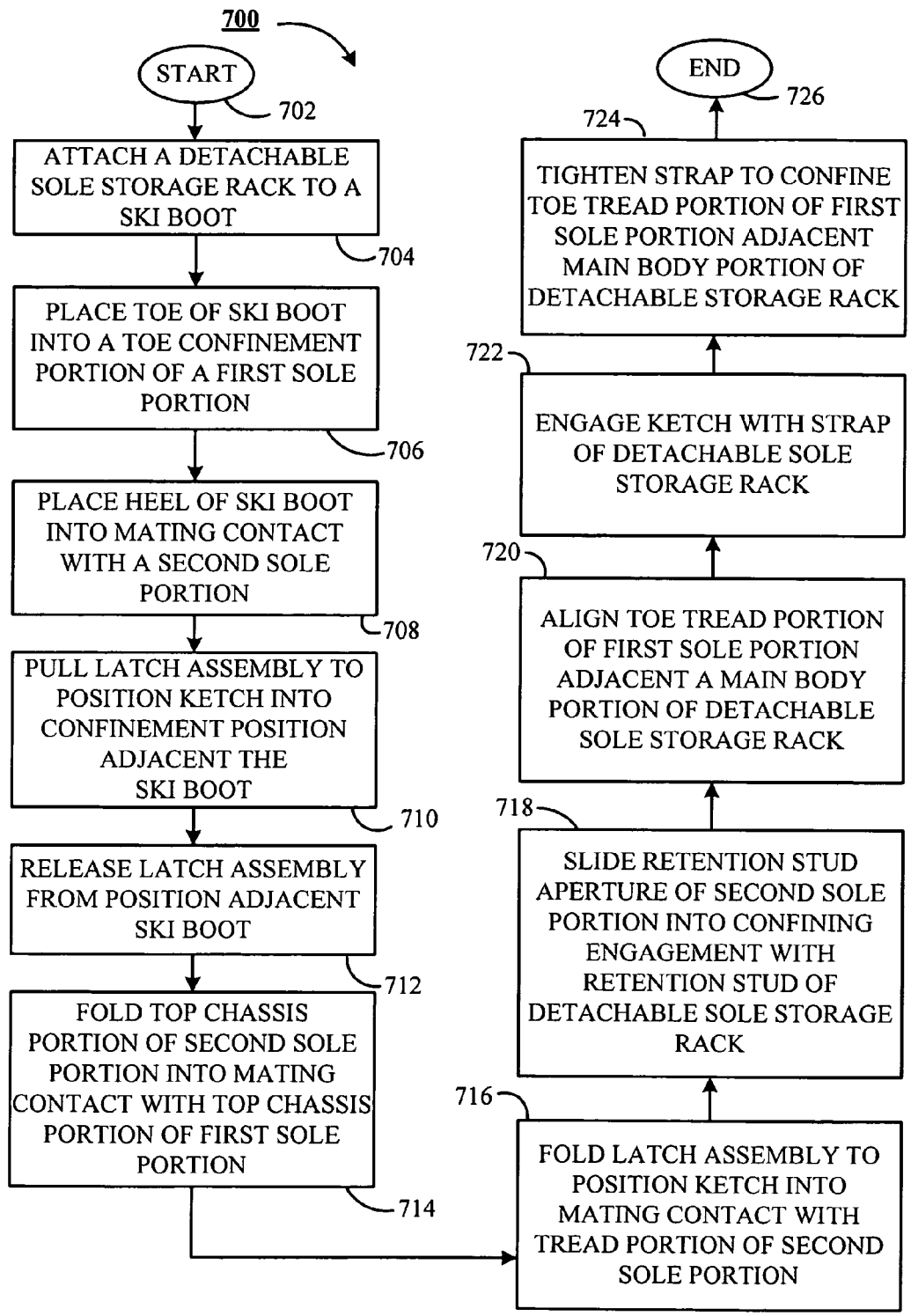
FIG. 24 is a flow diagram of a method of using the inventive combination of FIG. 22.

Flowchart 700 of FIG. 24, shows method steps of a process of using an inventive detachable sole (such as 530). The process commences at start step 702, and continues at process step 704. At process step 704, a detachable sole storage rack (such as 234), is attached to a ski boot (such as 220). At process step 706, a toe of a ski boot is placed into a toe confinement portion (such as 104) of a first sole portion (such as 122). At process step 708, a heel of the ski boot is placed in mating contact with a second sole portion (such as 124). At process step 710, a latch assembly (such as 532) is pulled to position a catch (such as 504), of the latch assembly into a confinement position adjacent the ski boot.

At process step 712, the latch assembly is released from a position adjacent the ski boot to detach the detachable sole from the ski boot. At process step 714, a top chassis portion (such as 162) of the second sole portion, is folded into mating contact with a top chassis portion (such as 154) of the first sole portion. At process step 716, the latch assembly is folded to position the catch into mating contact with a heel tread portion (such as 134), of the second sole portion. At process step 718, a pair of retention stud apertures (such as 230), are slid into confining engagement with a pair of chassis retention studs (such as 232). At process step 720, a toe tread portion (such as 133), of the first sole portion is aligned adjacent a main body portion (such as 236) of the detachable sole storage rack.

The catch is lashed with a strap (such as 260) to the detachable storage rack at process step 722. At process step 724, the strap is tightened to confine the toe tread portion of the first sole portion adjacent the main body portion of the detachable storage rack, and the process concludes at end process step 726.

With respect to the above description, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

It will be clear that the present invention is well adapted to attain the ends and advantages mentioned as well as those inherent therein. While presently preferred embodiments have been described for purposes of this disclosure, numerous changes may be made which will readily suggest themselves to those skilled in the art and which are encompassed by the appended claims.

What is claimed is:

1. A combination comprising:
    an ankle and foot covering; and
    a detachable sole configured for attachment to and detachment from said ankle and foot covering, wherein said detachable sole comprises;
        a chassis that includes a baffled support matrix interposed between top and bottom chassis portions;
        a toe confinement portion secured to said baffled support matrix and configured for confinement of baffled support matrix adjacent said ankle and foot covering;
        a latch assembly attached to said baffled support matrix and configured for securement of baffled support matrix adjacent said ankle and foot covering, in which said ankle and foot covering comprises a contoured heel portion, and in which said latch assembly comprises:
            a catch configured to conform to said contoured heel portion, a catch support interacting with said catch;
            a chassis attachment member communicating with said chassis; and
            an adjustment member interposed between said catch support and said chassis attachment member, wherein said adjustment member accommodates a snug conformance of said catch adjacent said heel portion.

2. The combination of claim 1, in which said ankle and foot covering comprises a toe portion of predetermined shape, and in which said toe confinement portion comprises a free standing shape, wherein said free standing shape is altered to accommodate said predetermined shape upon an engagement of said toe confinement portion by said toe portion.

3. The combination of claim 2, in which said toe portion is formed from a quasi pliable polymer.

4. The combination of claim 1, in which said catch support comprises:
    a catch mount portion;
    an alignment portion projecting from said catch mount portion; and
    a first threaded portion communicating with said alignment portion wherein said threaded portion is configured for interaction with said adjustment member.

5. The combination of claim 4, in which said catch support further comprising a hinge portion interposed between said alignment portion and said first threaded portion to form said communication between said alignment portion and said threaded portion.

6. The combination of claim 1, in which said chassis attachment member comprises:
    a chassis mount portion;
    an extension portion projecting from said chassis mount portion; and
    a second threaded portion communicating with said extension portion wherein said second threaded portion is configured for interaction with said adjustment member.

7. The combination of claim 4, in which said chassis mount portion further comprising an attachment aperture adjacent said chassis, and a fastener passing through said attachment aperture and communicating with said chassis to secure said chassis mount portion rotatably aligned adjacent said chassis.

8. The combination of claim 1, in which said adjustment member comprises a coiled spring.

9. The combination of claim 8, in which said catch support comprises a first threaded portion, said chassis attachment member comprises a second threaded portion, wherein each said first and second threaded portions provide female threads for interaction with said coil spring, and wherein said coil spring comprises a continuous coil, wherein said continuous coil provides a continuous male thread, which interacts with corresponding female threads of said first and second threaded portions to couple said catch support to said chassis attachment member.

10. The combination of claim 9, in which said ankle and foot covering substantially immobilizes an ankle supporting said ankle and foot covering.

11. The combination of claim 10, in which said ankle and foot covering comprises an orthopedic device.

12. The combination of claim 10, in which said ankle and foot covering comprises a ski boot.

13. The combination of claim 12, further comprising a storage rack configured for attachment to said ski boot and for supporting said detachable sole when said storage rack is attached to said ski boot and said detachable sole is detached from said ski boot.

14. The combination of claim 13, in which said storage rack comprises:
    a main body portion configured for mating conformance with said toe tread portion of said toe chassis portion;
    a hook adjustment portion projecting from a proximal end of said main body portion;
    an attachment member confined by said hook adjustment portion and positionably adjustable relative to said hook adjustment member;
    a chassis support projecting from a distal end of said main body portion;
    a chassis retention stud extending from said chassis support shelf, said stud interacting with said toe chassis portion to position said toe tread portion adjacent said main body portion;
    a main body support extending from a mid-portion of said main body portion;
    a strap support member projecting from said proximal end of said main body portion, and wherein a garment confinement slot is formed between said hook adjustment portion and said strap support member a strap pin attached on a distal end of said strap support member; and a strap attached to said strap pin, said strap interacting with said latch body to confine said toe tread portion adjacent said main body portion.

15. A method by steps comprising:

attaching a detachable sole storage rack to a ski boot;

placing a toe of said ski boot into a toe confinement portion of a first sole portion;

positioning a heel of said ski boot into mating contact with a second sole portion;

pulling a latch assembly to position a catch of said latch assembly into a confinement position adjacent said ski boot;

releasing said catch from said confinement position adjacent said ski boot to detach said detachable sole from said ski boot;

folding a top chassis portion of said second sole portion into mating contact with a top chassis portion of said first sole portion;

articulating said latch assembly to position said catch into mating contact with said tread portion of said second sole portion;

sliding a retention stud aperture of said second sole portion into confining engagement with a retention stud of said detachable sole storage rack;

aligning a toe tread portion of said first sole portion adjacent a main body portion of said detachable sole storage rack;

engaging said catch with a strap of said detachable sole storage rack; and tightening said strap to confine said toe tread portion of said first sole portion adjacent said main body portion of said detachable sole storage rack to form a combination ski boot with attached detachable sole storage rack storing the detachable sole.

* * * * *